US00PP24128P2

(12) United States Plant Patent
Tas

(10) Patent No.: US PP24,128 P2
(45) Date of Patent: Dec. 31, 2013

(54) ***ALSTROEMERIA* PLANT NAMED 'TESSUNLIGHT IMPROVED'**

(50) Latin Name: *Alstroemeria hybrida*
Varietal Denomination: Tessunlight Improved

(75) Inventor: Marius Tas, De Kwakel (NL)

(73) Assignee: Vof Hortipartners, Heerhugowaard (NL)

( * ) Notice: Subject to any disclaimer, the term of this patent is extended or adjusted under 35 U.S.C. 154(b) by 96 days.

(21) Appl. No.: 13/385,279

(22) Filed: Feb. 10, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Susan McCormick Ewoldt
(74) *Attorney, Agent, or Firm* — C. A. Whealy

(57) ABSTRACT

A new and distinct cultivar of *Alstroemeria* plant named 'Tessunlight Improved', characterized by its upright and uniformly mounding plant habit; sturdy and strong plants; moderately vigorous growth habit; yellow-colored flowers with short pedicels; and good garden performance.

1 Drawing Sheet

Botanical designation: *Alstroemeria hybrida.*
Cultivar denomination: 'TESSUNLIGHT IMPROVED'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Tessunlight Improved'.

The new *Alstroemeria* plant is a product of a planned breeding program conducted by the Inventor in Heerhugowaard, The Netherlands. The objective of the breeding program is to create new potted garden *Alstroemeria* plants that flower continuously and have attractive leaf and flower coloration.

The new *Alstroemeria* plant is a naturally-occurring branch mutation of *Alstroemeria hybrida* 'Tessunlight', not patented. The new *Alstroemeria* plant was discovered and selected by the Inventor on a single flowering plant from within a population of plants of 'Tessunlight' in a controlled greenhouse environment in Heerhugowaard, The Netherlands in June, 2008.

Asexual reproduction of the new *Alstroemeria* plant by root divisions in a controlled greenhouse environment in Heerhugowaard, The Netherlands since September, 2008 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tessunlight Improved'. These characteristics in combination distinguish 'Tessunlight Improved' as a new and distinct *Alstroemeria* plant:

1. Upright and uniformly mounding plant habit.
2. Sturdy and strong plants; moderately vigorous growth habit.
3. Yellow-colored flowers with short pedicels.
4. Good garden performance.

Plants of the new *Alstroemeria* can be compared to plants of the mutation parent, 'Tessunlight'. Plants of the new *Alstroemeria* differ from plants of 'Tessunlight' in the following characteristics:

1. Plants of the new *Alstroemeria* are larger and more vigorous than plants of 'Tessunlight'.
2. Plants of the new *Alstroemeria* have larger flowers than plants of 'Tessunlight'.

Plants of the new *Alstroemeria* can be compared to plants of the *Alstroemeria hybrida* 'Staprisara', disclosed in U.S. Plant Pat. No. 14,080. In side-by-side comparisons, plants of the new *Alstroemeria* differ primarily from plants of 'Staprisara' in flower color as plants of 'Staprisara' have yellow and red purple bi-colored flowers. In addition, plants of the new *Alstroemeria* are more vigorous than plants of 'Staprisara'.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant. The photograph comprises a side perspective view of a typical flowering plant of 'Tessunlight Improved' grown in a container.

DETAILED BOTANICAL DESCRIPTION

The aforementioned photograph and following observations and measurements describe plants of the new *Alstro-*

*emeria* grown during the winter in 4.6-liter containers in a glass-covered greenhouse in Kudelstaart, The Netherlands. During the production of the plants, day temperatures ranged from 14° C. to 16° C. and night temperatures ranged from 12° C. to 14° C. Plants were 15 weeks old when the photograph and description were taken. Color references are made to The Royal Horticultural Society Colour Chart, 2007 Edition, except where general terms of ordinary dictionary significance are used.

Botanical classification: *Alstroemeria hybrida* 'Tessunlight Improved'.

Parentage: Naturally-occurring branch mutation of *Alstroemeria hybrida* 'Tessunlight', not patented.

Propagation:

*Type*.—By root divisions.

*Time to produce a rooted young plant, summer*.—About seven weeks at 20° C.

*Time to produce a rooted young plant, winter*.—About eight weeks at 16° C.

*Root description*.—Fibrous, fleshy; up to 2 cm in thickness; white in color.

*Rooting habit*.—Freely branching; medium density.

Plant description:

*Plant and growth habit*.—Upright and uniformly mounded habit; freely branching habit with about 19 primary lateral branches developing per plant, dense and bushy appearance; sturdy and strong plants; moderately vigorous growth habit.

*Plant height*.—About 23.8 cm.

*Plant diameter* (*area of spread*).—About 41 cm.

Lateral branch description:

*Aspect*.—Mostly upright to somewhat outwardly spreading.

*Length*.—About 12.4 cm.

*Diameter*.—About 5 mm.

*Internode length*.—About 8 mm.

*Strength*.—Moderately strong.

*Texture*.—Smooth, glabrous.

*Color*.—Close to 144B with a dull outer layer, close to 144A.

Foliage description:

*Arrangement*.—Alternate; below the peduncles in a single whorl; simple.

*Length*.—About 5.7 cm.

*Width*.—About 3.2 cm.

*Shape*.—Ovate to broadly lanceolate.

*Apex*.—Acute.

*Base*.—Cuneate.

*Margin*.—Entire.

*Texture, upper and lower surfaces*.—Smooth, glabrous.

*Venation pattern*.—Parallel.

*Color*.—Developing leaves, upper surface: Close to 145A. Developing leaves, lower surface: Close to 145A. Fully expanded leaves, upper surface: Close to N138B; venation, close to 144A. Fully expanded leaves, lower surface: Close to N137A; venation, close to 144B.

*Petioles*.—Length: About 2.2 cm. Diameter: About 1 mm to 7 mm. Color: Close to 143A to 143B.

Flower description:

*Flower type and habit*.—Single zygomorphic flowers arranged in compound umbels; flowers face mostly outwardly; perianth segments separate; freely flowering habit with about ten flowers per inflorescence and about 190 flowers developing per plant.

*Natural flowering season*.—Plants begin flowering about eight weeks after planting; flowering continuous from early April through the summer in The Netherlands.

*Fragrance*.—None detected.

*Flower longevity on the plant*.—About ten days; flowers not persistent.

*Flower buds*.—Length: About 4.2 cm. Diameter: About 1.4 cm. Shape: Narrowly obovate. Color: Proximal half, close to 145C to 145D; distal, close to 147B to 147C.

*Umbel height*.—About 12 cm.

*Umbel diameter*.—About 14.3 cm.

*Flower diameter*.—About 7.9 cm.

*Flower depth* (*height*).—About 6.6 cm.

*Perianth*.—Arrangement: Six arranged in two whorls, each whorl with two lateral and one median segments. Size, inner perianth: Length, lateral segments: About 6.4 cm. Width, lateral segments: About 2.6 cm. Length, median segment: About 5.7 cm. Width, median segment: About 2.7 cm. Size, outer perianth: Length, all segments: About 6.5 cm. Width, all segments: About 4.8 cm. Shape, inner perianth, lateral and median segments: Narrowly obovate. Shape, outer perianth, lateral and median segments: Obcordate. Apex, inner perianth, lateral and median segments: Abruptly acute. Apex, outer perianth, lateral and median segments: Broadly retuse with a small abruptly acute point. Base, inner and outer perianths, lateral and median segments: Attenuate or cuneate. Margin, inner and outer perianths, lateral and median segments: Entire. Texture, inner and outer perianths, lateral and median segments: Smooth, glabrous. Color, inner perianth: When opening, all segments, upper surface: Close to 3B to 3C; towards the apex, close to 155C; apex, close to 144B; spots and streaks, close to 187A. When opening, all segments, lower surface: Close to 3D; towards the apex, close to 155C; apex, close to 144B; spots and streaks, close to 177B to 177C. When opening, median segment, lower surface: Close to 4D; towards the apex, close to 155C; apex, close to 144B; spots and streaks, close to 177B to 177C. Fully opened, lateral segments, upper surface: Close to 7A to 7B; towards the apex, close to 155C; apex, close to 144B; spots and streaks, close to 187A; color does not change with development. Fully opened, median segment, upper surface: Close to 7C; towards the apex, close to 155C; apex, close to 144B; spots and streaks, close to 187A; color does not change with development. Fully opened, lateral segments, lower surface: Close to 12B; towards the apex, close to 155C; apex, close to 144B; central spot, close to 63C to 63D; spots and streaks, close to 177B to 177C; color does not change with development. Fully opened, median segments, lower surface: Close to 10B; towards the apex, close to 155C; apex, close to 144B; spots and streaks, close to 187A; color does not change with development. Color, outer perianth: When opening, all segments, upper surface: Close to 155B to 155C; towards the base, close to 155A; apex, close to 138B; few spots and streaks, close to 187A. When opening, all segments, lower surface: Close to 155C; towards the base, close to 155A; apex, between 138B and 144C to 144D. Fully opened, all segments, upper surface: Close to NN155B; towards the base, close to 10B; towards the apex, close to 195C to 195D; apex, close to 138B; color does not change with development. Fully opened, all segments, lower surface: Close to NN155C to NN155D; towards the apex and central band, close to 144C slightly tinged with close to 63C to 63D; apex, close to 138B; color does not change with development.

*Pedicels*.—Length: About 1.3 cm. Diameter: About 2 mm. Strength: Moderately strong. Angle: Erect to about 30° from vertical. Texture: Smooth, glabrous. Color: Close to 144B.

*Reproductive organs*.—Stamens: Quantity per flower: Six. Filament length: About 4.2 cm. Filament color: Close to NN155B; towards the base, close to 157C. Anther shape: Oblong to elliptical. Anther length: About 8 mm. Anther color: Close to 152A to 152B. Pollen amount: Moderate. Pollen color: Close to 153D. Pistils: Quantity per flower: One. Pistil length: About 5 cm. Style length: About 4.3 cm. Style color: Close to NN155C to NN155D. Stigma shape: Tri-parted; parts, club-shaped, curved. Stigma color: Close to NN155C to NN155D. Ovary color: Close to 146D tinged with close to 200D.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind and rain. Plants of the new *Alstroemeria* have been observed to tolerate high temperatures of about 35° C. and to be hardy to USDA Hardiness Zone 8.

It is claimed:

1. A new and distinct *Alstroemeria* plant named 'Tessunlight Improved' as illustrated and described.

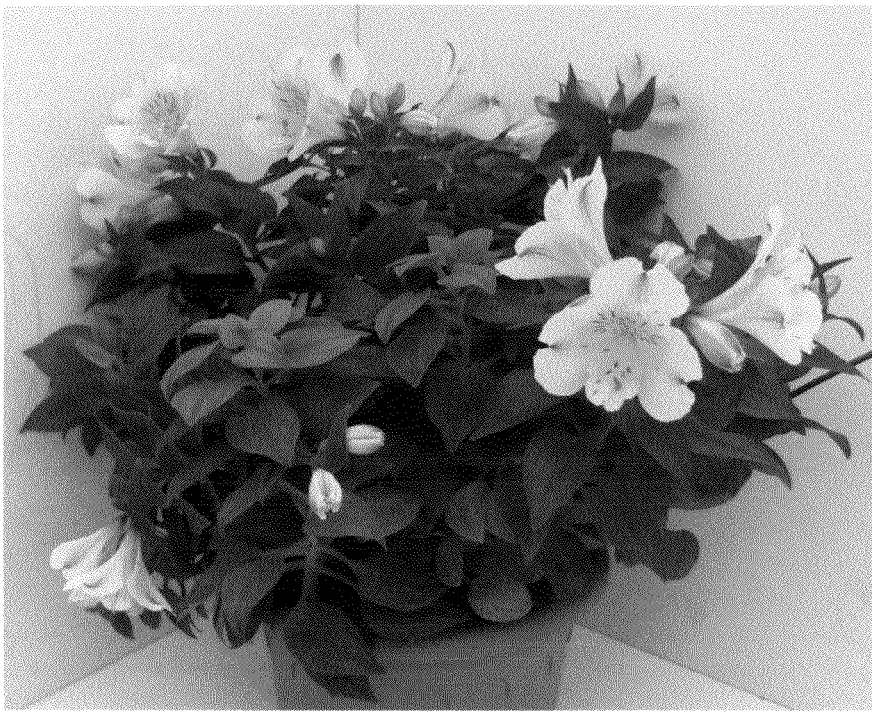

* * * * *